United States Patent
Frank

(10) Patent No.: US 6,693,537 B2
(45) Date of Patent: Feb. 17, 2004

(54) STORAGE TRAY

(76) Inventor: Ruth Frank, 24 Kimberly Dr., Durham, NC (US) 27707

(*) Notice: Subject to any disclaimer, the term of this patent is extended or adjusted under 35 U.S.C. 154(b) by 167 days.

(21) Appl. No.: 09/866,640

(22) Filed: May 30, 2001

(65) Prior Publication Data

US 2002/0179484 A1 Dec. 5, 2002

(51) Int. Cl.$^7$ ............................................. G08B 13/14
(52) U.S. Cl. .................. 340/568.1; 340/566; 340/571; 340/572.1; 340/691; 705/2; 705/3; 206/557; 206/561; 206/581; 206/564; 206/5; 206/83; 206/438; 206/63.5
(58) Field of Search .............................. 340/568.1, 566, 340/571, 572.1, 691; 705/2, 3; 206/217, 541, 557, 561, 570, 581, 564, 5, 83, 438, 63.5

(56) References Cited

U.S. PATENT DOCUMENTS

| | | | |
|---|---|---|---|
| 3,623,651 A | | 11/1971 | Marcan |
| 3,811,566 A | | 5/1974 | Bateman |
| 3,987,267 A | * | 10/1976 | Moore .......................... 219/728 |
| 4,106,624 A | | 8/1978 | Thurman |
| 4,217,476 A | * | 8/1980 | Bellavoine ................... 219/725 |
| 4,754,883 A | * | 7/1988 | Grzywa ........................ 224/400 |
| 5,239,491 A | * | 8/1993 | Mucciacciaro .............. 702/177 |
| 5,383,411 A | | 1/1995 | Tomaka et al. |
| 5,405,004 A | | 4/1995 | Vest et al. |
| 5,775,507 A | * | 7/1998 | Wood .......................... 206/581 |
| 6,116,165 A | | 9/2000 | Kadesky |
| 6,116,425 A | | 9/2000 | Frayer et al. |
| 6,138,831 A | * | 10/2000 | Agostinelli .................. 206/541 |
| 6,294,999 B1 | * | 9/2001 | Yarin et al. ............... 340/573.1 |
| 6,445,299 B1 | * | 9/2002 | Rojas, Jr. .................. 340/573.1 |

OTHER PUBLICATIONS

2000 National Student Design Competition and Design for the Millennium Home, International Housewares Show, Jan. 16–19, 2000, Chicago, Illinois.

2001 Housewares Design Center International Housewares Show, Jan. 14–17, Chicago, Illinois.

Brochure—Hill–Rom NetLinx, "Raising the Standards in Healthcare Information and Communication", Hill–Rom, Cary, NC.

\* cited by examiner

*Primary Examiner*—Daniel J. Wu
*Assistant Examiner*—Tai T. Nguyen
(74) *Attorney, Agent, or Firm*—Dickstein Shapiro Morin & Oshinsky LLP

(57) ABSTRACT

A personal item storage tray which includes a storage surface that incorporates a personal item identification, placement, retention, storage and removal apparatus or structure. One embodiment includes a substantially planar arrangement of depressions or recessed compartments designed to receive specific personal items such as, for example, eyeglasses, hearing aids and dentures. The compartments may be uniquely designed, shaped and marked to signal the uses of the compartment and to distinguish each compartment from the other to aid in visual identification and discrimination between the uses of each recessed compartment. The presence of items in the compartments is used to signal to the users of the tray that items are accounted for and not missing. The bottom surface of the tray includes a non-skid surface to avoid accidental or undesirable lateral movement. The tray is designed with a moldable or shapeable material. The tray has personal item inventory and management automation features and devices incorporated into its body to assist nursing staff or other users in accounting for personal items. Such inventory or missing item notification automation features includes a system having timers, sensors, and alerting signaling devices. These devices detect the presence of personal items within the tray storage areas and sound, signal or emit a missing item indication. The staff or other users of the tray are alerted to the necessity to search for a missing item when the tray signal system is activated.

2 Claims, 6 Drawing Sheets

STORAGE TRAY

FIELD OF THE INVENTION

This invention relates to the field of portable trays used for storage purposes. Specifically, the invention relates to the identification, placement, retention, storage, removal and/or accounting of personal items belonging to individuals, such as patients.

BACKGROUND OF THE INVENTION

Portable trays have become widely used to facilitate easy access to items placed on the tray. Common applications include bed trays, tool trays, medical trays and the like.

Some tray designs have focused on a planar storage or object placement surface that is substantially parallel with the ground and that is capable of a high degree of portability. Trays in use in assisted living (AL), nursing home (NH) or long term care (LTC).

AL, NH or LTC facilities, for example, have a flat surface which is used for general non-specific temporary storage. Placement, securing and repetitive identification and mental association with the tray of personal items by AL, LTC or NH patients and residents is not easily accomplished on the flat tray surfaces.

Staff members of AL locations, LTC facilities or nursing homes have noted a high loss rate of personal items by frail or demented residents or patients (hereinafter "residents"). Residents living in nursing homes have various mental and physical impairments which affect their ability to store and retrieve personal items. Residents with moderate to severe physical or mental impairments commonly misplace, damage or discard personal items essential to daily life. Examples of frequently lost essentials include dentures, eye glasses and hearing aids. The loss of personal items has resulted in an under utilization of such items, diminishing the quality of life for AL, LTC and NH residents.

AL, LTC or NH residents, for example, commonly receive assistance from at least three shifts of caregivers each day, with rotation of staff to cover weekends and holiday periods. The sheer number of different people involved with placing, removing, storing and cleaning residents' essential personal items such as eyeglasses, hearing aids and dentures creates the likelihood that there will be inconsistencies in how these items are stored and managed. For example, staff from the night or morning shift will typically assist with morning grooming, when eyeglasses, dentures and hearing aids usually would be worn or used. Evening shift staff assist with the preparation for bed, when assistive devices would typically be stored for the night. Differences in storage habits cause one set of shift workers to look in places logical to them but illogical to the preceding or following staff. This inconsistency creates difficulty for staff and residents in locating the mislaid or lost items. Such differences in storage choices and logic also detract from the staff's ability to determine if items have been mislaid and initiate a search for lost items quickly.

Safety issues are also a very significant concern in the use of technology. AL, LTC and NH residents, for example, have disabilities or medical conditions necessitating equipment or appliances that is safe for their use in light of their inability to physically or mentally exercise a normal standard of precaution and care when using equipment or facilities. Many possible applications of modern technology or existing equipment is too complex or physically demanding for AL, LTC or NH residents. Normal abilities are not within many residents' capabilities to grasp an item or prevent themselves from falling or refraining from pushing on an item or piece of equipment. Thus, adaptive equipment must be designed with numerous safety and accident prevention features. Features which prevent the tray from slipping when pushed or being easily broken when dropped onto the floor are important. Design considerations also must anticipate residents dropping the tray onto themselves or others. The existing storage and tray designs do not address the physical and mental limitations of many patients, including AL, LTC and NH residents. These also lack the required safety research as well as critical safety and utilization features absolutely necessary for successful use in, for example, an AL, LTC or NH environment.

Existing tray designs also lack features which allow for the mental comprehension difficulties that many patients, including AL, LTC and NH residents, experience. While existing tray designs are uniform in appearance, design and/or shape, they do not clearly signal to a resident or staff member that a personal item (eyeglasses, for example) should be placed in a particular receptacle. The lack of easily found reference points for storing personal items has resulted in confusion and substantial difficulties for frail and demented residents attempting to engage in routine daily living activities. Also, the lack of special and well defined receiving receptacles increases the difficulty for staff to introduce or teach a routine and clearly understood pattern of storage and retrieval to patients.

The continuing lack of standard and well understood personal item storage trays continues to waste staff time in item searches and generate substantial costs due to the need to replace lost items. Residents and patients suffering from physical or mentally debilitating conditions lose the use of personal items required to participate in daily life activities resulting in a lower quality of life. Thus, a need exists for a portable and safe personal item storage tray that is designed for use by patients, residents and staff. This invention is designed to address, among other things, such needs.

BRIEF SUMMARY OF THE INVENTION

The present invention provides for a novel tray which is used for personal item identification, storage, retention, removal and management. The tray surface is substantially planar with an arrangement of personal item storage features. The invention uses personal item identification, placement, retention, storage and removal features and devices which facilitate the management of personal items by residents, patients and staff. The devices and features incorporate three or more depressions or recessed compartments (hereinafter "compartments") designed to receive specific personal items which can include eyeglasses, hearing aids and dentures. The storage, retention and removal features or devices are uniquely shaped and marked to distinguish each compartment from the other for ease in visual identification and discrimination between the uses of each feature or device. In the exemplary invention, recessed compartments have markings which visually associate personal items with said compartments. Any means for accomplishing storage or retention of personal items which can be used to secure, store or attach personal items to the tray can be used as well.

The bottom surface, sides, interior or surfaces of the tray includes a non-skid surface or other devices or structures which immobilize the tray or inhibit or prohibit accidental or undesirable lateral movement. The tray is incorporated into other structures as well to facilitate the function of personal item management.

The tray has a weighted base to assist with prevention of accidental displacements or movements of the tray. Such weights are part of the base itself or can be components such as batteries or other personal inventory automation components distributed in such a way to ensure easy balancing of the tray when it is at rest or being moved.

One embodiment of the tray includes personal item inventory and management automation features and devices incorporated into the tray body which assist nursing staff or other users in accounting for personal items. Such inventory or missing item notification automation features include a system which uses timers, mechanical linkages, pressure sensors, item sensors, light emitting diode emitter/detector trigger circuits, control circuits and/or alerting signaling devices such as mechanical flagging indicators, alerting lights, alerting sounds, passive or active transponder signals or any other electronic signals which, in combination with the sensor system, detect the presence of personal items within the tray storage areas and sound, signal or emit a missing item indication if an item is not present under predetermined circumstances. The staff or other users of the tray are alerted to the necessity to search for a missing item when the tray signal system is activated. The present invention can also use any other component or system which detects the presence of personal items which are desired to be in the tray compartments or storage means and signals to staff, patients or residents that the item is missing.

DETAILED DESCRIPTION OF THE INVENTION

The present invention includes a storage surface that incorporates personal item identification, placement, retention, storage and removal features, components or devices. Said components or devices are designed to facilitate staff, residents or patients management of personal items. However, it is important to note that this invention can be used in any environment where the storage of personal items occurs. Personal items are defined as items which are needed to engage in basic daily routine living activities considered essential to a person, such as a resident or a patient's quality of life. These living activities include reading, eating or interacting with others. The present invention also can incorporate various safety and personal item automation features or components. It is important to note that the present invention can also incorporate any items including those not considered personal items such as tissue paper holders, watches, jewelry, etc.

Figure 1:
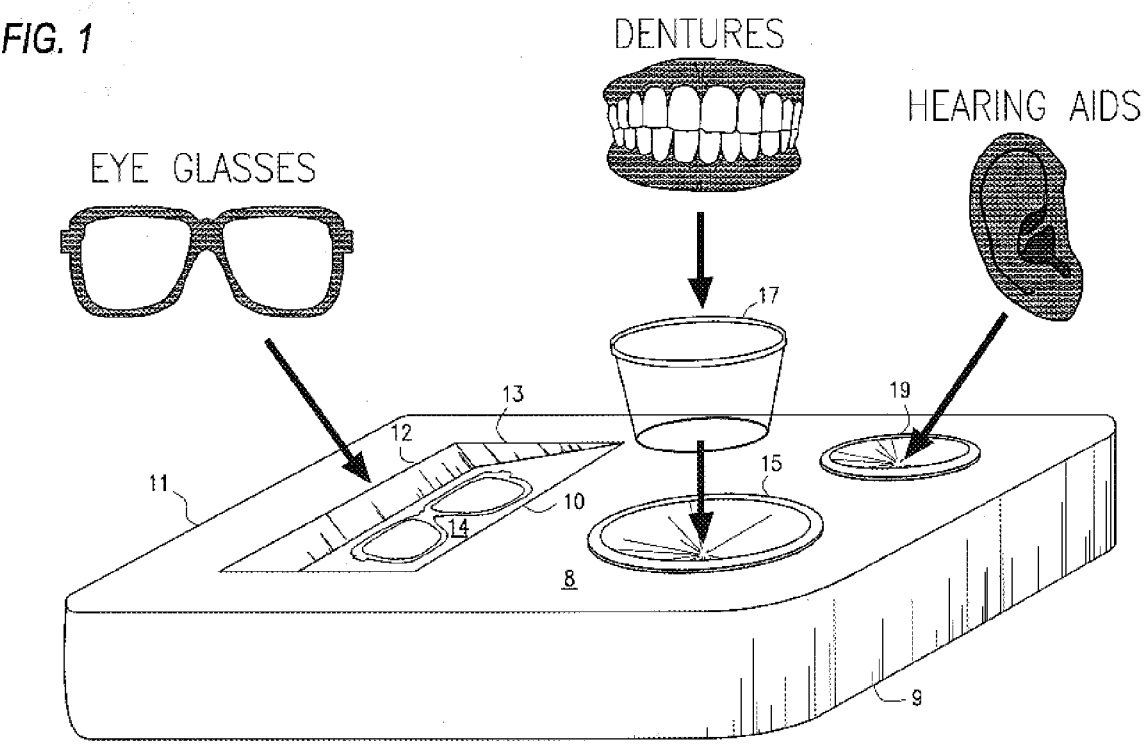
FIG. 1 is a perspective view of a first embodiment of the storage tray items. In this Figure, the embodiment is shown storing eyeglasses, dentures and hearing aids.

FIG. 1 discloses one embodiment of the storage tray for personal items such as eyeglasses, dentures and hearing aids consisting of a substantially planar surface 8 that has compartments placed upon and extending below its surface toward its base 9. The tray assembly example is rectangular in shape with a base extending below the top surface. The embodiment in FIG. 1 shows the tray body having three compartments.

The tray can be designed with a moldable or shapeable material such as plastic, rubber or vinyl for ease of cleaning and resistance to damage from rough handling. Any lightweight rigid material or any material and structural design which facilitates the personal storage function, supports the personal item placement, retention, storage and retrieval components and facilitates ease of cleaning and resistance to damage from rough handling can also be used to accomplish the function of the present invention.

The embodiment 11 described in FIG. 1 shows the first recessed compartment 13. Compartment 13 is elongated and rectangular in shape with a depressed bottom that inclines downward from surface 8 toward base 9 along the innermost lengthwise side 10 of the recessed compartment towards the outside widthwise side of the tray 12. The first compartment's 13 bottom 14 runs downward at an angle with respect to the planar surface. The first compartment's 13 bottom 14 is ramped and recessed sufficiently to permit the secure storage or retention of the eyeglasses within the compartment. The storage compartment 13 is designed to facilitate the removal of eyeglasses from the compartment through the ramping or tapering of the compartment bottom permitting the eyeglasses to be slid from the compartment, then grasped and removed. The first compartment's depth is such that eyeglasses are far enough below the planar surface 8 to ensure that they do not easily shift up or slide out of the tapered or slanted bottom. The eyeglasses compartment 13 can be designed to permit many varieties of eyeglass and eyeglass case depths which vary depending on eyeglass style, size and construction. The tray's manufacture may also be varied to account for different end-use storage specifications, customers or intended users. An alternative embodiment can also contain a case or container built into the tray for eyeglasses or other personal items.

The second compartment 15 is cylindrical in shape and extends from the tray's planar surface 8 to a convenient distance below. The depth should be suitable for receiving a standard sized denture cup shaped container, cup, receptacle or container designed to contain dentures. The invention is provided with a removable denture cup 17 of standard size which can be removed, cleaned and filled with water when dentures are placed into the cup. Dentures can be placed directly into the tray receptacle as well, but use of the cup is desirable and preferable for hygiene and health reasons. The cup is not restricted to dentures. It can be conveniently used for any form of storage including contact lenses, dental floss, or any other item desired.

The exemplary third compartment 19 is cylindrical in shape and extends from the tray's top planar surface 8 to a depth suitable to receive hearing aids and extra hearing aid batteries.

All compartments are dimensioned to receive personal items such as eyeglasses, dentures and hearing aids. Compartment dimensions can also be designed to accommodate storage cases or containers for personal items such as, for example, eyeglass cases and hearing aid cases or other similar size containers, as chosen by the user.

Compartments 13, 15 and 19 are placed in relation to each other in such a manner as to create even spacing between the compartments and the sides of the tray. Location of the compartments can also be accomplished to accommodate personal item inventory automation components as will be disclosed below or to facilitate the addition of other components which are desirable for use on a personal item storage tray. Examples of such components (not shown) include hand grips, texture strips, electronic components, signaling devices, additional compartments, additional or alternative item retention features, or any other device which accomplishes the function of personal item storage, tray usage, personal item inventory, or tray and item management. Also the automation of any or all of the aforesaid and below discussed tasks, features or functions is contemplated by the present invention.

The storage or retention systems used by the present invention are designed to aid or facilitate in the placement, retention, storage and removal of personal items on a tray or surface by the staff, residents and/or patients, for example, in AL, NH or LTC facilities or locations where personal item management or use can occur. Any feature, method, component or process which aids in the placement, retention, storage, retrieval and/or removal of personal items can be used to accomplish the functions of the present invention. It is important to note that any retainer, storage or storage and sorting system, design or apparatus which a designer or practitioner engaging in the design of storage trays or personal item storage systems can also be used to accomplish the present invention's function of personal item storage associated with a tray. Velcro, Velcro straps, straps, strings, buckles, snaps, ties, interference fits or enclosures, covers, screens, binders, compartments, elastic envelopes, rigid sliding covers, flexible sliding covers, magnets or electromagnets on the tray as well as the personal item, tapes, bars, strips, elastic bands, adhesives, hooks, adhesives which adhere only to a specific coating which is applied to the tray and personal items or any other securing device, method, substance or process can also be used besides the examples shown by the figures and discussed in the application to accomplish the function of secure personal item storage. Accordingly, the embodiments discussed above and below should not be understood to be the only ways to accomplish the placement, retention, storage, retrieval and/or removal functions of the present invention.

Referring to FIG. 1, the base of the tray 9 extends downward perpendicularly from the tray's planar surface 8 far enough to provide suitable distance or intervening space from the top of the planar surface 8 or floor of the storage compartments and the bottom of the tray 9. The lower surface of the tray base is designed to provide maximum contact with a supporting surface when lateral movement restriction or maximization of tray stability is desired (as will be described further below).

Figure 2:
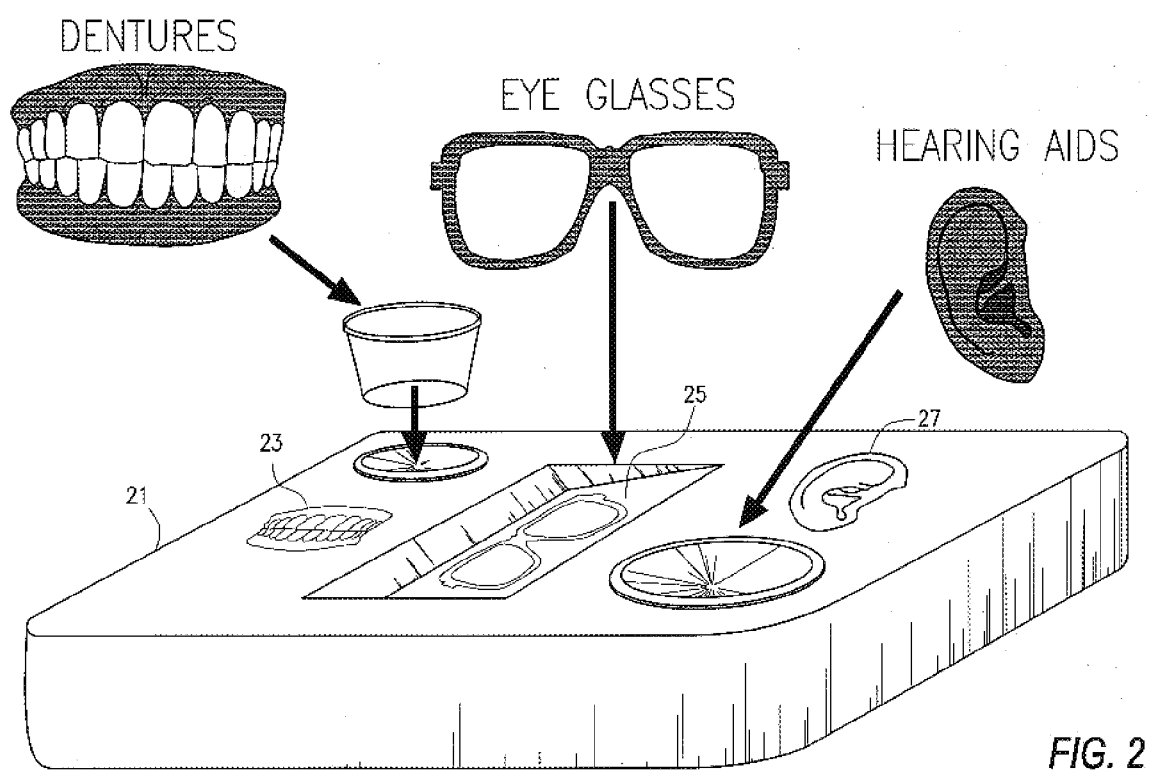
FIG. 2 is a perspective view of a second embodiment the storage tray.

In the second embodiment shown in FIG. 2, the invention is designed identically to the invention as described in the first embodiment except as to the placement of the compartments and their labeling. FIG. 2 shows labels or identifying marks (23, 25 and 27) next to their corresponding compartments 13, 15 and 19. Labels correspond to the personal item which is intended to be stored in the compartment (with the exception of the eyeglasses compartment which is labeled in the same manner as shown in the first embodiment).

The labeling of compartments is designed to facilitate staff, resident and patient identification of the uses for each compartment. For example, a label can consist of a picture of a set of dentures (FIG. 2, element 23) applied next to or on the bottom of a storage compartment or device. A patient or resident is thus able to associate the identifying feature or label design with the actual personal item which should be placed in a given compartment or storage feature, component or device. Design considerations for identification or labeling of placement, storage, retention, retrieval or removal assemblies, components or compartments can include user, staff, resident or patient mental and physical capabilities, expected wear created by rough handling, cultural factors, safety issues and languages used. Color coding of compartments or any other design which aids patients or residents in associating said personal item retention with corresponding retrieval device, components or compartments as well as distinguishing between compartments can also be used to facilitate ease of compartment identification and use. Personal items or any item stored on the tray can also have a color code or other identifying mark or device added to them which can be used as an aid to determining the proper location on the tray for each personal item.

The third embodiment of the present invention includes some or all of the above mentioned features as well as a weighted base. The weighted base is employed to ensure the tray is not easily knocked over or pushed off a surface such as a table. The weighted base may or may not be used in a particular environment or set of patients depending on a number of factors, including whether the patients using the tray tend to be physically aggressive or mentally deficient as to make the use of the tray unsafe, or whether the patients in question tend to behave in a manner that makes the advantages of a weighted tray outweigh the disadvantages.

Figure 3:
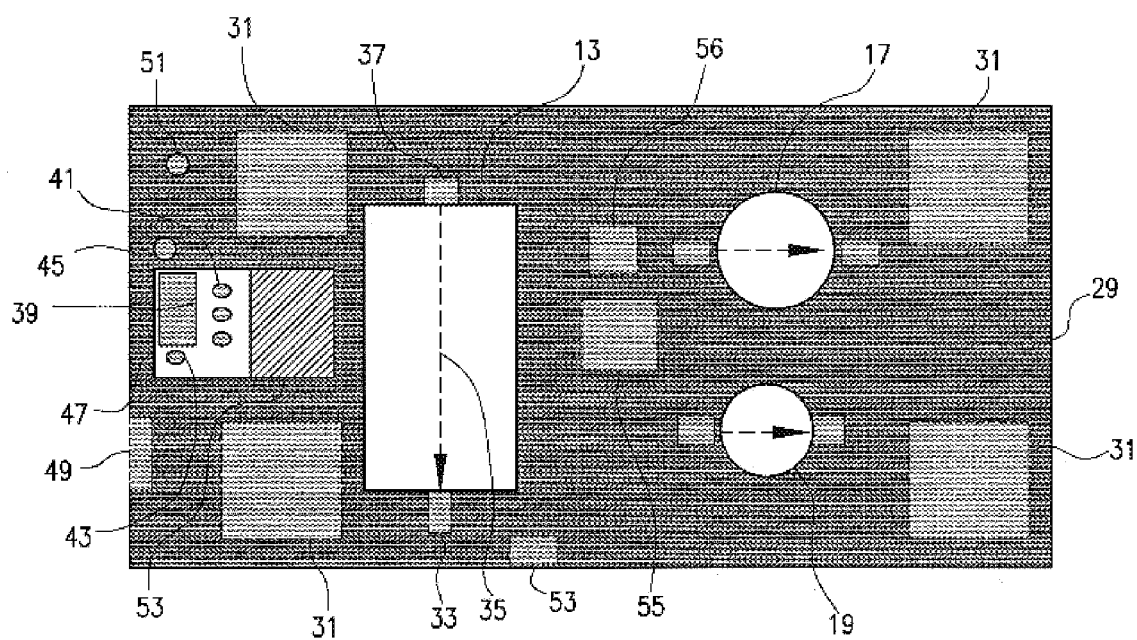
FIG. 3 is a top view of a third embodiment of the invention with automation features.

FIG. 3 describes a fourth embodiment of the present invention which can include all or some of the features described above or below as well as devices that facilitate the storage and inventory functions of the tray such as, for example, a means to assist staff with automation of inventory and accounting for personal items. Such means can include sensing units or other automatic sensor devices built into the tray which manually or electronically report an alarm or a missing item condition.

FIG. 3 illustrates an embodiment of a missing personal item sensing and signaling system incorporated within the storage tray. This embodiment discloses the use of light beam sensor components which includes a light beam emitter 37 with a focusing apparatus emplaced into a side wall of each compartment with a light beam detector 33 positioned on the opposite wall of said compartment to receive the emitted light beam 35. The light beam emitter 37 can be any light source including, but not limited to, an LED or other light emission device. The detector 33 can, for example, consist of a cadmium sulfide (CdS) cell, a detector lens assembly and a detector assembly housing unit. The emitter beam 35 is aligned on the opposing vertical wall of the personal item storage compartment (FIG. 4, items 37, 35, and 33) to ensure the emitted light beam is focused on the detector lens assembly 33. The detector lens assembly focuses the light beam into a bright spot on the surface of the CdS cell. If a colored LED is used in the transmitter, a piece of glass or transparent plastic of the same color can be placed on the CdS cell or other detection mechanism to filter out undesirable light which interferes with the detector's function.

An embodiment of the tray can include a personal item detection and alarm control circuit 55 which is activated by a clock/timer 47 input signal which can be set for shift change times by use of a display unit 39 and configuration buttons 41. The control circuit 55 and sensor system will sense if all required personal items are present on the tray 29 by activating the light beam emitter and detector units (37 and 33). If the light beam 35 is blocked, then the control circuit 55 will detect a beam blocked condition indicating all items are in the appropriate slots when a timer or clock signal input is received by the control unit 55. If the control unit 55 inputs signify all personal items are present, no action is taken and the system powers down with the exception of the clock/timer system 47. If an item is missing, then a beam "not blocked" condition will be detected. Control circuit 55 will then activate at least one warning or missing item notification device. FIG. 3 includes two possible warning or missing item notification devices including a speaker unit 49 to emit an audible signal and a light or LED 51 to emit a visual signal. The audible and/or visual signals trigger a staff response that a staff member is required to deactivate as the staff member performs inventory activities. The missing item notification system can also employ any system which alerts a person or staff member.

An embodiment of the tray can also include various event sensing systems or timers. The timer/sensors can be installed into the tray to trigger sensing mechanisms which detect if personal items are stored in the tray compartments when certain light conditions exist. For example, a portable infrared beam contained in a handheld emitter unit can be waved across or focused onto an alternative embodiment tray to trigger the sensing mechanism (which includes an infrared sensor unit by staff or other automation systems employed to activate sensing units).

The tray embodiment disclosed by FIG. 3 also includes a dropped or impact detection apparatus 56. Unit 56 which transmits a signal to the control circuit 55 when an significant impact or dropped condition is detected A staff response will be triggered to investigate the reason for the alarm or notification signal being emitted by the speaker 49 or light emitting system 51 on the tray 29. Detector 56 may be an important safety device, since a patient dropping the tray may need immediate medical assistance.

Figure 4:
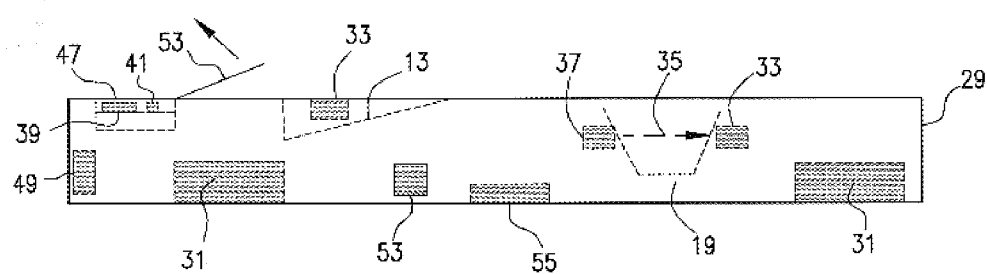
FIG. 4 is a side view of the third embodiment of the personal item storage tray shown in FIG. 3.
Figure 5:
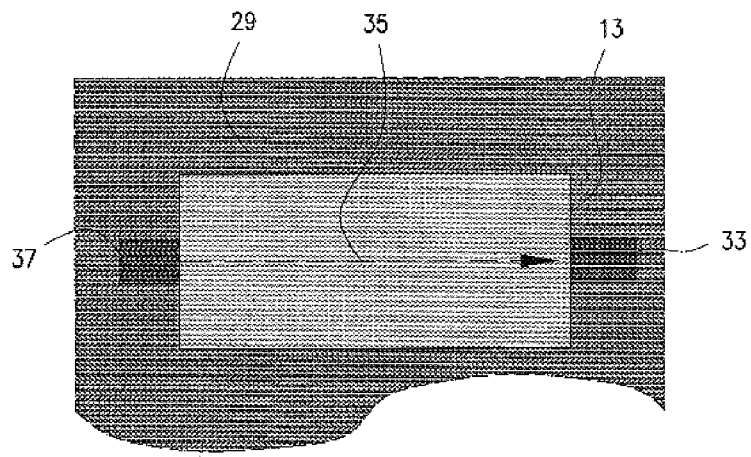
FIG. 5 is a top view of an exemplary storage compartment used in the embodiment shown in FIGS. 3 and 4.
Figure 6:
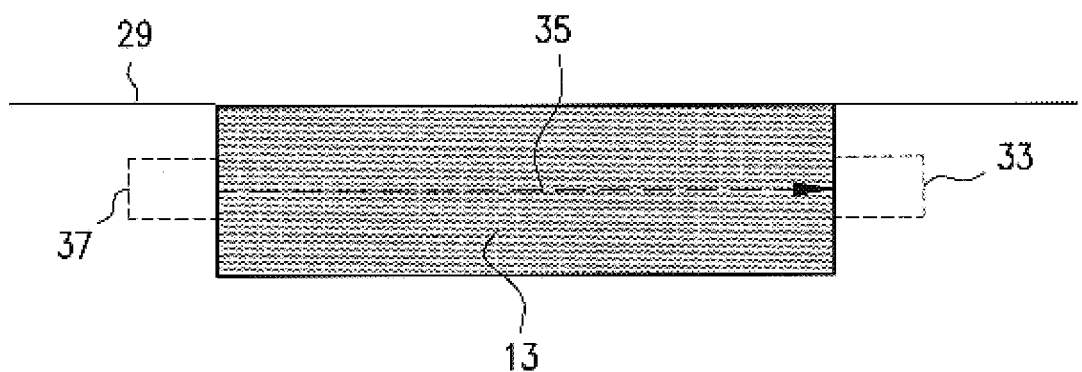
FIG. 6 is a side view of an exemplary personal item storage compartment shown in FIG. 5.

In the embodiment disclosed by FIGS. 3 and 4, a staff member will be required to deactivate the alarm or notification signals by use of the alarm deactivation switch button 43. The tray disclosed by FIG. 3 also incorporates a locking feature 45 which is used to secure the timer/clock assembly 47 compartment. Other possible sensing devices can also be used in conjunction or in combination with the present invention to perform these same functions and activate an appropriate warning or missing item notification system in a manner similar to the functions described above for the light beam detection unit. Other embodiments can also include alternative means or apparatus which activate or deactivate the missing item alarm or notification signals or systems.

FIG. 4 shows a side view of the embodiment disclosed in FIG. 3. This Figure shows the timer/clock assembly 47 to be recessed below the surface of the displayed tray 29. This embodiment includes a timer/clock assembly 47 within the recessed compartment displayed by FIG. 4 which can be covered and protected by a hinged lid assembly 53. The hinged lid can be swung into a closed position or an open position. The lid 53 also corresponds to a locking unit 45 which is disclosed in FIG. 3. The locking unit 45 can be used to secure the timer/clock assembly 47 to prevent accidental or intentional tampering with the setting buttons 41 or activation of the alarm cut-off 43.

Other embodiments can include features which vary the capabilities of the missing item detection and notification system. One addition includes a feature which transmits a missing item condition signal to a central receiving station or computer the presence or absence of items in each compartment. Additional controls can also be added to vary the type and detection timing of individual personal item sensing units. Sensing units can also consist of passive transponders attached to each personal item stored on the tray. These types of sensing units are commonly used to track laboratory samples, pets, tools, warehouse stock, industrial waste containers and other movable items. The readers (or sensing units for passive transponders) for the sensing units can be incorporated into the tray. Sensing devices can also include pressure or other sensors in each compartment or personal item retention or storage features or devices which are used to detect the presence or absence of a personal item in a corresponding tray compartment. Mechanical linkages can be incorporated into the tray design to raise or lower mechanical flags on the tray. These flags are activated in response to mechanical pressure sensors in the tray. Finally, visual indicators can be incorporated into the tray which are exposed or hidden mechanically or via electrical components by the presence or absence of personal items in the tray personal item receptacles.

FIGS. 3 and 4 also disclose a battery 31 or energy storage systems that are used as means for providing a weighted base to the storage tray system. A battery system 31 is installed in such a manner to reduce damage from impacts as well as ensuring the tray is balanced. One or more batteries can be positioned in the case in the center, equidistant from each battery or in any manner which results in a center of gravity which lies in the center of the tray assembly and does not interfere with any other tray structure. A charging system as well as battery condition indicator can be installed on the tray assembly. FIGS. 3 and 4 also disclose a tray which includes a plug-in power receiver system 53 which can be connected to an alternating current power supply which, for example, could be found in facility wall electric sockets.

Tray usage information can be stored in computer storage devices in the tray as well. Personalized information can also be associated with each tray such as, for example, resident or patient name and storage item descriptions and serial numbers. Such personalized information can be stored manually or electronically in a database.

Figure 7:
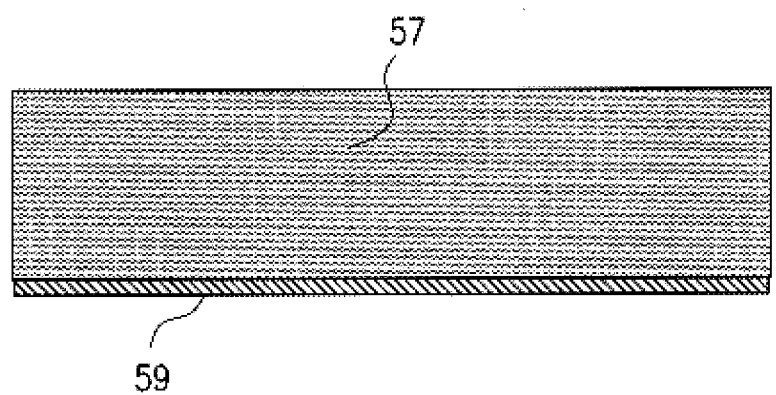
FIG. 7 is a side view of an exemplary tray body with anti-skid or high friction co-efficient material attached or applied to the bottom surface of the tray embodiment.

FIG. 7 discloses a non-skid surface 59 embodiment which is applied to the bottom or other locations of the tray. The lower outer surface of the tray base or storage surface support system can be equipped or coated with a non-skid, friction or movement restriction coating or layer 59. The non-skid or movement restriction layer 59 or surface can include a rubber or other applied material which provides a high coefficient of friction to the bottom of the tray assembly creating an increased gripping or friction capability to reduce slipping and sliding of the tray on a surface (such as those typically found in AL, LTC or NH environments). The non-skid surface can be designed to interact only with another specially designed coating surface which sticks or adheres only between the two materials. The non-skid bottom surface can be designed with many types of materials. Those materials include rubber or other non-abrasive materials which avoid damage to the surface the tray is placed upon. If desired, a surface such as Velcro® can be substituted on the tray and the tray supporting surface. Movement restriction devices can also be attached to the sides, bottom, stands or other supporting or receiving components which the tray is placed upon in order to perform the function of inhibiting or prohibiting undesired, unintentional or accidental lateral movement or other undesirable movement. Other non-skid features can include any scheme or application which prevents or restrains accidental or undesirable movement.

Figure 8:
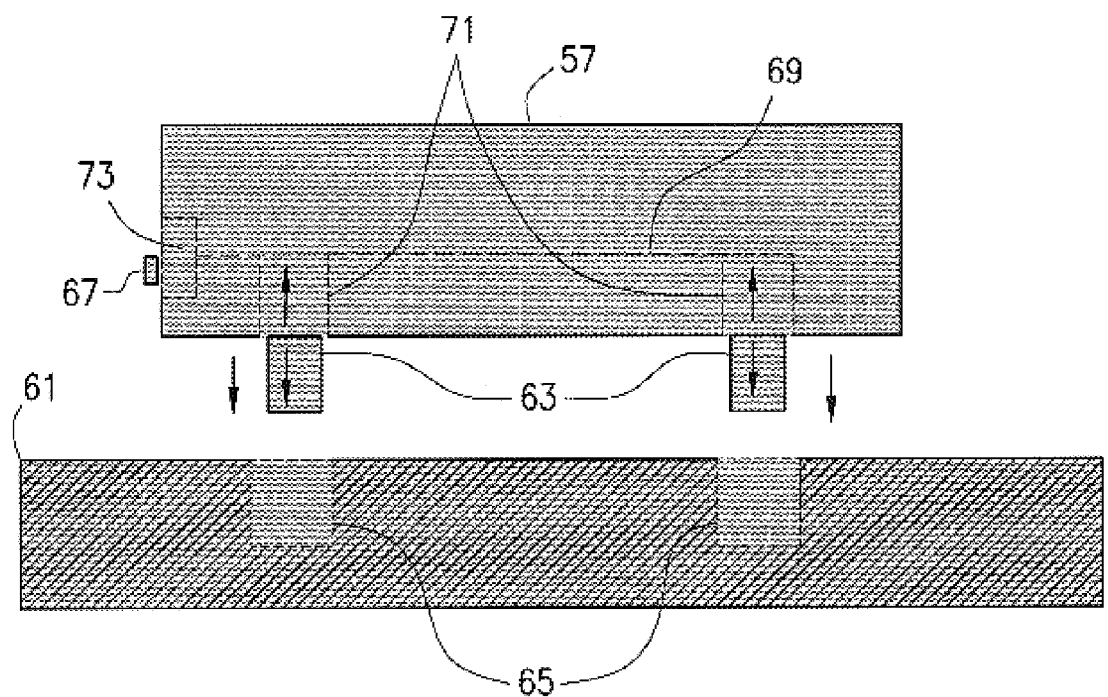
FIG. 8 is a lengthwise, or long side, view of an exemplary tray assembly which discloses an alternative embodiment of the undesirable or accidental movement inhibitor, restriction or immobilization function of the present invention using an insertion peg and mounting surface system.

FIG. 8 discloses an alternative embodiment of the immobilization or movement restraining or prohibition function of the present invention in the form of retractable insertion pegs 63. The peg system disclosed in this embodiment includes a peg extension actuator button 67 installed on a width, or shorter, side of the tray body 57. This embodiment's insertion pegs 63 are housed in the retractable peg housing assembly 71 when fully retracted. The pegs 63 are spring or pressure-loaded by a mechanism which is a part of the housing unit 71. The pegs 63 are extended when the retractable peg release button 67 is pressed. The actuation of the button activates the retractable peg release control mechanism 73 which in turn actuates a mechanical or electromechanical linkage system 69. The linkage 69 triggers a release mechanism within the housing units 71.

FIG. 8 shows how the extended pegs are inserted into receiving peg insertion holes 65 placed into or installed within a mounting or supporting surface 61 which the tray 57 is placed upon. The lateral or undesirable movement restraining system or function in this embodiment is activated when the tray 57 and pegs 63 are extended and inserted within the receiving holes 65.

Figure 9:
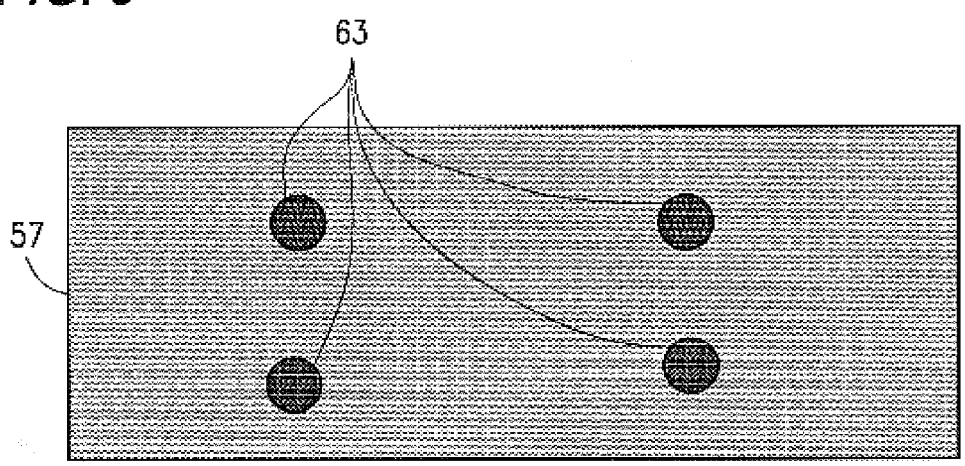
FIG. 9 is a bottom view of the embodiment described in FIG. 8 disclosing an embodiment of the peg system.

FIG. 9 discloses a plan view of the tray's bottom surface 57 which is described in the embodiment of FIG. 8. This view shows four pegs 63 used to secure the tray 57 to the mounting surface 61.

Any system which can be used to immobilize or position the tray in any of its possible embodiments can be used to perform the function of temporary tray immobilization. Such immobilization or support systems can position the tray horizontally or vertically or any combination thereof. If vertical positions are utilized, then alternate embodiments of the personal item placement, storage, retention, removal or retrieval features, structures or devices will be used to ensure said items are easily placed, stored, retained and/or retrieved by AL, NH and LTC patients or residents using non horizontal orientations or configurations of the tray assembly.

Other embodiments of the invention can incorporate more complex features such as micro-processor and memory storage to track the use of personal items and store information in a database system. Other embodiments can also include systems which use databases containing item storage information.

What is claimed as new and desired to be protected by Letters Patent of the United States is:

1. A tray comprising:

a storage surface;

a plurality of personal item storage structures extending below said storage surface, said storage structures adapted to receive a different one of said personal items, said personal items comprising eyeglasses, hearing aids and a denture container;

a supporting structure formed underneath said storage surface, said supporting structure adapted to prevent movement of said tray;

one or more personal item placement identification portions formed onto a lower surface inside at least one said storage structures; and a plurality of personal item presence sensing portions, at least part of said presence sensing portions are formed into one or more sides of at least one said storage structures, said presence sensing portions comprising a signal mechanism to indicate that one or more personal items are not present in at least one said storage structures.

2. The tray of claim 1 further comprising:

a movement sense mechanism and alert signal mechanism which triggers and communicates an alarm signal when the tray is dropped.

* * * * *